United States Patent
Jacoby et al.

(10) Patent No.: US 10,899,694 B2
(45) Date of Patent: Jan. 26, 2021

(54) DEHYDROGENATION REACTION

(71) Applicant: Firmenich SA, Satigny (CH)

(72) Inventors: Denis Jacoby, Geneva (CH);
Jean-Jacques Riedhauser, Geneva (CH); Philippe Miranda, Bernex (CH); Harvey Randall, Geneva (CH); Fabrice Keller, Geneva (CH)

(73) Assignee: Firmenich SA, Satigny (CH)

( * ) Notice: Subject to any disclaimer, the term of this patent is extended or adjusted under 35 U.S.C. 154(b) by 144 days.

(21) Appl. No.: 16/307,665

(22) PCT Filed: Jun. 26, 2017

(86) PCT No.: PCT/EP2017/065714
§ 371 (c)(1),
(2) Date: Dec. 6, 2018

(87) PCT Pub. No.: WO2018/001963
PCT Pub. Date: Jan. 4, 2018

(65) Prior Publication Data
US 2019/0345088 A1 Nov. 14, 2019

(30) Foreign Application Priority Data
Jun. 27, 2016 (EP) ..................................... 16176358

(51) Int. Cl.
*C07C 45/65* (2006.01)
*B01J 23/00* (2006.01)
*B01J 23/44* (2006.01)
*C07C 67/317* (2006.01)
*C07C 49/597* (2006.01)
*C07C 49/603* (2006.01)
*C07C 49/637* (2006.01)
*C07C 69/738* (2006.01)

(52) U.S. Cl.
CPC .............. *C07C 45/65* (2013.01); *B01J 23/44* (2013.01); *C07C 67/317* (2013.01); *C07C 49/597* (2013.01); *C07C 49/603* (2013.01); *C07C 49/637* (2013.01); *C07C 69/738* (2013.01); *C07C 2601/10* (2017.05); *C07C 2601/16* (2017.05); *C07C 2602/28* (2017.05)

(58) Field of Classification Search
CPC .................................. B01J 23/44; C07C 45/65
See application file for complete search history.

(56) References Cited

U.S. PATENT DOCUMENTS

| 4,538,009 | A  | 8/1985 | Goetz et al.     |
| 6,433,229 | B1 | 8/2002 | Fischer et al.   |
| 6,586,620 | B1 | 7/2003 | Crawford et al.  |
| 7,495,132 | B2 | 2/2009 | Walsdorff et al. |

FOREIGN PATENT DOCUMENTS

EP          0123233 A2   10/1984

OTHER PUBLICATIONS

Zhang et al. Reaction-activated palladium catalyst for dehydrogenation of substituted cyclohexanones to phenol and H2 without oxidants and hydrogen acceptors. Chemical Science, vol. 6, 4674-4680. (Year: 2015).*
Diao et al. Aerobic Dehydrogenation of Cyclohexanone to Cyclohexenone Catalyzed by Pd (DMSO)2 (TFA)2: Evidence of Ligand-Controlled Chemoselectivity. Journal of the American Chemical Society, vol. 135, 8205-8212. (Year: 2013).*
International Search Report and Written Opinion for international application No. PCT/EP2017/065714 dated Aug. 7, 2017.
Chapuis et al., "Synthesis of cis-Hedione® and methyl jasmonate via cascade Baylis-Hillman reaction and Claisen ortho ester rearrangement", Helv. Chim. Acta, 2005, vol. 88, No. 12, pp. 3069-3088.
Diao et al., "Direct aerobic α,β-dehydrogenation of aldehydes and ketones with a Pd (TFA ) 2/4,5-diazafluorenone catalyst", Chem. Sci., 2012, vol. 3, n° 3, pp. 887-891.
Mori et al., "Unexpected Pd-catalyzed hydrogenation of phenol to 2-cyclohexene-1-one: enhanced activity and selectivity assisted by molecular oxygen", Chem. Commun., 2012, vol. 48, pp. 8886-8888.
Theissen, R. J., "A new method for the preparation of α,β-unsaturated carbonyl compounds", J. Org. Chem., 1971, vol. 36, No. 6, pp. 752-757.

* cited by examiner

*Primary Examiner* — Sikarl A Witherspoon
(74) *Attorney, Agent, or Firm* — Armstrong Teasdale LLP

(57) ABSTRACT

The present invention relates to the field of organic synthesis and more specifically it concerns a process for the dehydrogenation of compound of formula (I) catalyzed by palladium ($Pd^0$) in elemental metallic form.

16 Claims, No Drawings

DEHYDROGENATION REACTION

RELATED APPLICATIONS

This application is a national stage application under 35 U.S.C. § 371 filing of International Patent Application PCT/EP2017/065714 filed 26 Jun. 2017, which claims the benefit of EP Patent Application no 16176358.6 filed 27 Jun. 2016.

TECHNICAL FIELD

The present invention relates to the field of organic synthesis and more specifically it concerns a process for the dehydrogenation of compound of formula (I) catalyzed by palladium (Pd).

BACKGROUND

Heterogeneous catalysis has been widely used in chemical industry to provide high-value compounds. In spite of a great excitement for this kind of catalysis, the heterogeneous dehydrogenation of a ketone to provide α,β-unsaturated ketone has been poorly reported. Such reactions have been conducted generally in gas phase; i.e. in very harsh conditions wherein the reaction temperature exceeds 350° C., as reported in U.S. Pat. No. 7,495,132. Not only, are such conditions incompatible with thermally unstable substrates but leads poor selectivity for unsymmetrical ketone.

Milder reaction conditions have been disclosed in *J. Org. Chem* 1971, 752 wherein dehydrogenation reaction is performed with homogeneous $Pd^{II}$ or $Cu^{II}$ catalyst. However said reaction conditions suffer from requiring large amount of unfriendly reagents and solvent. Moreover, the dehydrogenation of unsymmetrical ketone under said method provides a mixture of regioisomers wherein the formation of the less substituted double bond is favored.

So there is still a need to develop a regioselective, safe, practical and ecofriendly method to dehydrogenate unsymmetrical ketone, such as 2-pentylcyclopentan-1-one, or unsymmetrical and thermally unstable ketone, such as methyl 2-(3-oxo-2-pentylcyclopentyl)acetate, in order to synthesize the most substituted enone and in particular the most substituted cyclic enone. Such method allows gaining rapid access to building block which could be key intermediates toward more valuable compounds such as various quality of cis or trans methyl 2-(3-oxo-2-pentylcyclopentyl) acetate and mixture thereof being also known as Hedione® (trademark from Firmenich SA), Hedione® HC, Paradisone® (specific enantiomer of cis Hedione®, trademark from Firmenich SA). Said compounds are much appreciated perfumery ingredients, which are in general, obtained through an epoxide such as methyl 2-(5-acetoxy-1-pentyl-6-oxabicyclo[3.1.0]hexan-2-yl)acetate as disclosed in U.S. Pat. No. 6,586,620.

The present invention allows to obtain, by dehydrogenation under milder reaction conditions, the most substituted α,β-unsaturated ketone and in particular the most substituted α,β-unsaturated cyclic ketone with high regioselectivity and without decomposition of the starting ketone.

DESCRIPTION OF THE INVENTION

We have now discovered that the compounds of formula (I) can be produced in an advantageous manner by means of a dehydrogenation type reaction. Unexpectedly, the invention's process is performed in absence of hydrogen acceptor.

Therefore, a first object of the present invention is a process for the preparation of a compound of formula (I)

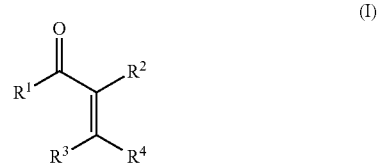

in a form of any one of its stereoisomers or a mixture thereof and wherein $R^1$, $R^2$ and $R^3$, simultaneously or independently, represent a linear or branched $C_{1-6}$ alkyl or alkenyl group or a linear $C_{2-5}$ alkynyl group, optionally comprising one or two functional groups selected amongst ether and ester; and $R^4$ represents a hydrogen atom, a linear or branched $C_{1-6}$ alkyl or alkenyl group or a linear $C_{2-5}$ alkynyl group, optionally comprising one or two functional groups selected amongst ether and ester; $R^1$ and $R^3$, taken together, represent a $C_{2-9}$ alkanediyl or alkenediyl group optionally substituted by one to two linear or branched $C_{1-5}$ alkyl or $C_{2-5}$ alkenyl groups; or/and $R^2$ and $R^4$, taken together, represent a $C_{2-9}$ alkanediyl or alkenediyl group optionally substituted by one to five linear or branched $C_{1-5}$ alkyl or $C_{2-5}$ alkenyl groups; or/and $R^3$ and $R^4$, taken together, represent a $C_{2-9}$ alkanediyl or alkenediyl group optionally substituted by one to two linear or branched $C_{1-5}$ alkyl or $C_{2-5}$ alkenyl groups;

comprising the step of dehydrogenate compound of the formula (II)

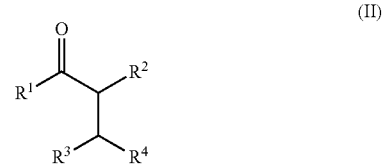

in a form of any one of its stereoisomers and wherein $R^1$, $R^2$, $R^3$ and $R^4$ have the same meaning as in formula (I); said dehydrogenation being performed under an inert atmosphere in the presence of Palladium ($Pd^0$) catalyst in elemental metallic form.

It is understood that by " . . . $R^1$ and $R^3$, taken together, represent a $C_{2-9}$ linear, branched or cyclic alkanediyl group or/and $R^2$ and $R^4$, taken together, represent a $C_{2-9}$ linear, branched or cyclic alkanediyl group or/and $R^3$ and $R^4$, taken together . . . " or the similar, that said group could form a (poly)cyclic alkyl group. In other words compound (I) could be acyclic, monocyclic or bicyclic, e.g. in the case wherein $R^1$ and $R^3$, as well as $R^3$ and $R^4$, are taken together, the compound of formula (II) comprises a bicyclic group such as a decalin, i.e. $R^1$, $R^3$ and $R^4$, taken together, represents an alkanetriyl.

According to any one of the above embodiments of the invention, said compounds of formula (II) are $C_6$-$C_{18}$ compounds.

According to any embodiments of the invention, and independently of the specific aspects, the compound (I) as well as the corresponding compound (II) can be in the form of any one of its stereoisomers or mixture thereof. For the sake of clarity by the term stereoisomer it is intended any diastereomer, enantiomer, racemate.

Indeed, the compound (I) or (II) may have stereogenic centers which can have different stereochemistry (i.e. when two stereogenic centers are present, compound (I) or (II) can have (R,R) or (R,S) configuration). Each of said stereogenic centers can be in a relative configuration R or S or a mixture thereof or in other words said compound of formula (II) or (I) can be in a form of pure enantiomer or diastereoisomer, or in a form of a mixture of stereoisomers.

According to any one of the above embodiments, said compound of formula (I) is compound of formula (III)

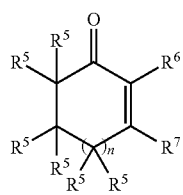

(III)

in a form of any one of its stereoisomers; wherein n is 0 or 1; $R^5$ groups represent, when taken separately, independently of each other, a hydrogen atom, a $C_{1-3}$ alkyl or alkenyl group; or two $R^5$ groups represent, when taken together, a $C_{1-5}$ alkanediyl or alkenediyl group optionally substituted by one to five linear $C_{1-3}$ alkyl groups; $R^6$ represents a linear or branched $C_{1-6}$ alkyl or alkenyl group or a linear $C_{2-5}$ alkynyl group, optionally comprising one or two functional groups selected amongst ether, and ester; $R^7$, represents a hydrogen atom, a linear or branched $C_{1-6}$ alkyl or alkenyl group or a linear $C_{2-5}$ alkynyl group, optionally comprising one or two functional groups selected amongst ether, and ester; $R^6$ and $R^7$, taken together, represent a $C_{2-9}$ alkanediyl or alkenediyl group optionally substituted by one to five linear or branched $C_{1-5}$ alkyl groups.

According to any one of the above embodiments, said compound of formula (II) is compound of formula (IV)

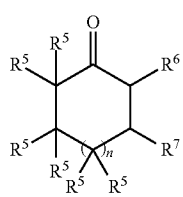

(IV)

in a form of any one of its stereoisomers; wherein n, $R^5$, $R^6$ and $R^7$ have the same meaning as in formula (III).

According to any one of the above embodiments, said compound of formula (I) is compound of formula (V)

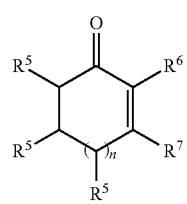

(V)

in a form of any one of its stereoisomers; wherein n is 0 or 1; $R^5$ represents a hydrogen atom, a $C_{1-3}$ alkyl or alkenyl group; $R^6$ represents a linear or branched $C_{1-6}$ alkyl or alkenyl group or a linear $C_{2-5}$ alkynyl group, optionally comprising one or two functional groups selected amongst ether, and ester; $R^7$, represents a hydrogen atom, a linear or branched $C_{1-6}$ alkyl or alkenyl group or a linear $C_{2-5}$ alkynyl group, optionally comprising one or two functional groups selected amongst ether, and ester; $R^6$ and $R^7$, taken together, represent a $C_{2-9}$ alkanediyl or alkenediyl group optionally substituted by one to five linear or branched $C_{1-5}$ alkyl groups.

According to any one of the above embodiments, said compound of formula (II) is compound of formula (VI)

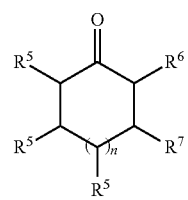

(VI)

in a form of any one of its stereoisomers; wherein n, $R^5$, $R^6$ and $R^7$ have the same meaning as in formula (III).

According to any one of the above embodiments, n is 0 or 1, preferably 0.

According to any one of the above embodiments, $R^5$ may represent a $C_{1-3}$ alkyl group. Preferably, $R^5$ may represent a hydrogen atom, a methyl, an ethyl, a propyl an isopropyl or propen-2-yl group or even more preferably a hydrogen atom, a methyl an ethyl or propen-2-yl group.

According to any one of the above embodiments, two $R^5$ groups, when taken together, represent a $C_{3-4}$ alkanediyl or alkenediyl group.

According to a particular embodiment, when n is 1, at least two $R^5$ group supported by the same carbon atom are different from hydrogen atom.

According to any one of the above embodiments, $R^6$ may represent a linear or branched $C_{1-6}$ alkyl group or a $C_{2-6}$ alkenyl group, optionally comprising one or two functional groups selected amongst ether, and ester. Preferably, $R^6$ may represent a methyl, an ethyl, a propyl an isopropyl, a butyl, a pentyl, a pentenyl, a hexenyl, a 1-methoxy-1-oxoheptan-3-yl or 3-methylbut-2-en-1-yl group. Preferably, $R^6$ may represent a methyl, an ethyl, a propyl an isopropyl, a butyl, a pentyl, a pentenyl, a hexenyl or 3-methylbut-2-en-1-yl group. Preferably, $R^6$ may represent a methyl or pentyl group or even more preferably a pentyl group.

According to any one of the above embodiments, $R^7$ may represent a hydrogen atom, a methyl, an ethyl or a propyl group or a $C_{1-3}$ alkyl acetate group. Preferably $R^7$ may represent a hydrogen atom, a methyl group or $C_{1-3}$ alkyl acetate group.

According to any one of the above embodiments, $R^6$ and $R^7$, taken together, represent a $C_{4-7}$ alkanediyl group optionally substituted by one to five linear $C_{1-3}$ alkyl groups. Preferably, $R^6$ and $R^7$, taken together, represent a $C_{5-6}$ alkanediyl group substituted by three to four linear $C_{1-2}$ alkyl group. Even more preferably, $R^6$ and $R^7$, taken together, represent a 2,3,4-trimethylpentane-2,4-diyl.

The compounds of formula (II) are commercially available or could be prepared by methods known in the art.

According to any above embodiment, the compound of formula (IV) may be, methyl 2-(3-oxo-2-pentylcyclopentyl) acetate, 3-methyl-2-pentylcyclopentan-1-one, 2-pentylcyclopentan-1-one, methyl 3-(2-oxocyclopentyl)heptanoate, 2,2,6-trimethylcyclohexan-1-one, 6-ethyl-2,2-dimethylcyclohexan-1-one, 2-ethyl-4,4-dimethylcyclohexan-1-one or 2,3,8a-trimethyloctahydronaphthalen-1(2H)-one. Preferably, the compound of formula (IV) is methyl 2-(3-oxo-2-pentylcyclopentyl)acetate, 3-methyl-2-pentylcyclopentan-1-one, methyl 3-(2-oxocyclopentyl)heptanoate or 2-pentylcyclopentan-1-one in a form of any one of their stereoisomers. Even more preferably, the compound of formula (IV) is methyl 2-(3-oxo-2-pentylcyclopentyl)acetate, 3-methyl-2-pentylcyclopentan-1-one or 2-pentylcyclopentan-1-one in a form of any one of their stereoisomers. Even more preferably, the compound of formula (IV) is methyl 2-(3-oxo-2-pentylcyclopentyl)acetate or 2-pentylcyclopentan-1-one in a form of any one of their stereoisomers. Even more preferably, the compound of formula (IV) is methyl 2-(3-oxo-2-pentylcyclopentyl)acetate in a form of any one of its stereoisomers.

According to any above embodiment, the compound of formula (III) may be methyl 2-(3-oxo-2-pentylcyclopent-1-en-1-yl)acetate, 3-methyl-2-pentylcyclopent-2-en-1-one, 2-pentylcyclopent-2-en-1-one, methyl 3-(5-oxocyclopent-1-en-1-yl)heptanoate, 2,6,6-trimethylcyclohex-2-en-1-one, 2-ethyl-6,6-dimethylcyclohex-2-en-1-one, 2-ethyl-4,4-dimethylcyclohex-2-en-1-one or 2,3,8a-trimethyl-4a,5,6,7,8,8a-hexahydronaphthalen-1(4H)-one. Preferably, the compound of formula (III) is methyl 2-(3-oxo-2-pentylcyclopent-1-en-1-yl)acetate, 3-methyl-2-pentylcyclopent-2-en-1-one, methyl 3-(5-oxocyclopent-1-en-1-yl)heptanoate or 2-pentylcyclopent-2-en-1-one. Even more preferably, the compound of formula (III) is methyl 2-(3-oxo-2-pentylcyclopent-1-en-1-yl)acetate, 3-methyl-2-pentylcyclopent-2-en-1-one or 2-pentylcyclopent-2-en-1-one. Even more preferably, the compound of formula (III) is methyl 2-(3-oxo-2-pentylcyclopent-1-en-1-yl)acetate or 2-pentylcyclopent-2-en-1-one. Even more preferably, the compound of formula (III) is methyl 2-(3-oxo-2-pentylcyclopent-1-en-1-yl)acetate.

According to any above embodiment, under the invention's process, an aromatic compound could be formed when n is 1. Said product could be converted into compound of formula (V) by method well-known in the art such as the one reported in Chem. Commun. 2012, 8886.

The invention's process is carried out in the presence of a catalytic amount of palladium (Pd$^0$) in elemental metallic form.

According to any one of the above embodiments of the invention, the invention' process may be performed without a pre-activation of the catalyst; e.g. heating the catalyst for several hours in the presence of hydrogen.

According to any one of the above embodiments of the invention, said palladium (Pd$^0$) is supported on a carrying material. Said carrying material may be acid, neutral or basic.

For the sake of clarity, by carrying material it is intended a material wherein it is possible to deposit such metal and which is inert toward the substrate.

According to any one of the above embodiments of the invention, specific and non-limiting examples of carrying material is carbon or aluminum oxide. Such supports are well known to a person skilled in the art. Preferably the palladium is supported on aluminum oxide or charcoal.

The supported palladium (Pd$^0$) is known compound and are commercially available. A person skilled in the art is able to select the preferred kind of metal as the way that it was deposit on the support, as the proportion of metal on support material, as the form (powder, granules, pellets, extrudates, mousses . . . ), as the surface area of the support and as the acidity or basicity of the catalyst.

According to any one of the above embodiments of the invention, the amount of metal relative to the support can range between 0.5% and 20% w/w, preferably between 0.5% and 10% w/w, or even preferably between 1% and 6%, relative to the weight on the support used.

According to any one of the above embodiments of the invention, the support material may be a mesoporous; i.e. the majority of pores are comprised between 2 to 50 nm; or microporous solid; i.e. the majority of pores are below 2 nm. Preferably, the average pores size is comprised between 5 and 15 nm and the pore volume is comprised between 0.15 to 0.50 mL/g. Said support material has a specific surface area (BET) comprised between 50 and 700 m$^2$/g, preferably comprised between 80 and 120 m$^2$/g.

According to any one of the above embodiments of the invention, the Palladium particles on the support have an average diameter comprised between 1 and 10 nm. The palladium dispersion may be comprised between 8 to 60%. The palladium particles may be mainly on edges of pores of the solid support (Eggshell distribution), or on edges of pores and deeper in pores (Mixed distribution) or uniformly distributed in pores (Uniform distribution).

The supported palladium (Pd$^0$) can be added into the reaction medium of the invention's process in a large range of concentrations. As non-limiting examples, one can cite as metal concentration values those ranging from 10 ppm to 200000 ppm, relative to the total amount of substrate. Preferably, the metal concentration will be comprised between 100 ppm to 10000 ppm, or even between 100 ppm and 500 ppm or 1000 ppm. It goes without saying that the process works also with more catalyst. However the optimum concentration of metal will depend, as the person skilled in the art knows, on the nature of the latter, on the nature of the substrate, if the process is run in batch or continuously and on the temperature, as well as the desired time of reaction.

The temperature at which the dehydrogenation can be carried out is comprised between 120° C. and 220° C. More preferably, the temperature at which the dehydrogenation can be carried out is comprised between 150° C. and 200° C., even more preferably, between 170° C. and 200° C. Of course, a person skilled in the art is also able to select the preferred temperature as a function of the melting and boiling point of the starting and final products as well as the desired time of reaction or conversion. The process of the invention allows to carry out the dehydrogenation under mild temperature condition which lead to decrease the amount of by-product in case of thermally unstable compounds such as methyl 2-(3-oxo-2-pentylcyclopentyl)acetate.

The reaction can be carried out in the presence or absence of a solvent. When a solvent is required or used for practical reasons, then any solvent current in such reaction type can be used for the purposes of the invention. Non-limiting examples include $C_{6-12}$ aromatic solvents such as 1,3-diisopropylbenzene or cumene or pseudocumene, $C_{9-16}$ alkane such as dodecane, oxygenated solvents like esters or ethers or mixtures thereof. The choice of the solvent is a function of the nature of the substrate and the person skilled in the art is well able to select the solvent most convenient in each case to optimize the reaction. Preferably, the reaction is conducted in absence of solvent; i.e. under neat conditions.

The invention's process can be carried out under batch or continuous conditions. Under continuous conditions, the dehydrogenation can be carried out at a higher temperature than under batch conditions. Under continuous conditions, the temperature may be comprised between 120° C. and 400° C. More preferably, the temperature at which the dehydrogenation can be carried out, under continuous conditions, is comprised between 150° C. and 300° C.

According to any one of the above embodiment the process of the invention is performed without bubbling oxygen in the reaction mixture. The process of the present invention is performed under inert atmosphere. By inert atmosphere, it is meant an atmosphere which does not contain gas participating to the reaction; e.g. any gas containing less than 10 wt % of oxygen, even less than 5 wt % of oxygen, even less than 1 wt % of oxygen. The inert atmosphere may be obtained by performing the reaction under an inert gas; e.g. nitrogen or argon. Alternatively, the inert atmosphere may be obtained by performing the reaction under a slight vacuum. Non limiting examples of slight vacuum may be a reaction performed at a pressure below or equal to 10000 Pa, even 5000 Pa, even 3000 Pa.

The invention's process is conducted in liquid phase. By the expression "the invention's process is conducted in liquid phase" it is meant the normal meaning in the art; i.e. the reaction mixture is mainly a liquid and not a gas. In other words, the invention's process is not performed in gas phase and the starting material is not evaporated to conduct the reaction.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Dehydrogenation of Compound of Formula (II) to Form Compounds of Formula (I) Under Batch Conditions In a flask equipped with magnetic stirrer, reflux condenser and Dean Stark apparatus, under inert atmosphere, compound of formula (II) (see Table 1) was stirred vigorously at a temperature indicated in Table 1 in the presence of 5% Pd/Alox (Noblyst 1148 Evonik, dry powder, Table 1) or 5% Pd/C (Hindustan, RD343, powder, 50% moisture, Table 1) over a period indicated in Table 1. The resulting suspension was cooled to 30° C. and the catalyst was filtered. After rinsing by acetone and evaporation of solvent to dryness, the crude was analyzed by GC (DB-1) showing the conversions into the compound of formula (I) having the most substituted double bond.

Under these conditions several compounds of formula (II) were tested. The results are reported in Table 1.

TABLE 1

Dehydrogenation of compound of formula (II) under batch conditions

| Compound of Formula (II) | Amount of Compound of Formula (II) (g) | Catalyst (% w/w) | T (° C.) | Time (h) | Conversion (% GC) | Selectivity (% GC) |
|---|---|---|---|---|---|---|
| 2,2-dimethyl-6-ethylcyclohexan-1-one | 10 | Pd/C (30) | 220 | 24 | 14.8 | 92[a] |
| methyl 2-(3-oxo-2-pentylcyclopentyl)acetate | 250 | Pd/Alox (5) | 180 | 22 | 24.4 | 97.9[b] |

[a] Main product was 2-ethyl-6,6-dimethylcyclohex-2-en-1-one. Other regioisomers such as regioisomer with an exo double bond; i.e. 6-ethylidene-2,2-dimethylcyclohexan-1-one, was not observed.
[b] Reaction performed under slight vacuum (3000 Pa). Main product was methyl 2-(3-oxo-2-pentylcyclopent-1-en-1-yl)acetate. Only trace amount of 3-methyl-2-pentylcyclopentan-1-one (0.1%), 3-methyl-2-pentylcyclopent-2-en-1-one (0.3%), methyl 2-(2-pentylcyclopentyl)acetate (0.05%) were observed.

Example 2

Dehydrogenation of Compound of Formula (II) to Form Compounds of Formula (I) Under Continuous Conditions In a 100 ml steel tubular reactor equipped with an electric oven, an ismatec pump, and a condenser, under inert atmosphere, compound of formula (II) (see Table 2) was up flowed in the liquid phase at ordinary pressure through 12 g of catalyst (4% Pd/C) at an average rate of 12 g/h and at temperature indicated in Table 2. The crude reaction mixture was cooled to 30° C. After rinsing by acetone and evaporation of solvent to dryness, the crude mixture was analyzed by GC (DB-1) showing the conversions into the compound of formula (I) having the most substituted double bond.

Under these conditions several compounds of formula (II) were tested. The results are reported in Table 2.

TABLE 2

Dehydrogenation of compound of formula (II) under continuous conditions

| Compound of Formula (II) | T (° C.) | Conversion (% GC) | Selectivity (% GC) |
|---|---|---|---|
| 2-pentylcyclopentanone | 320 | 16.3 | 78[a)] |
| 3-methyl-2-pentylcyclopentanone | 300 | 39 | 97[b)] |
| 3-methyl-2-pentylcyclopentanone | 320 | 52 | 97[b)] |
| 2,6,6-trimethylcyclohexanone | 320 | 16.3 | 78[c)] |
| 2-ethyl-6,6-dimethylcyclohexanone | 300 | 10 | 81[d)] |
| 2-ethyl-4,4-dimethylcyclohexanone | 300 | 7 | 55[e)] |
| 2,3,8a-trimethyloctahydronaphthalen-1-one | 340 | 9.5 | 85[f)] |

[a)] Main product was 2-pentylcyclopent-2-en-1-one. Other regioisomers such as regioisomer with an exo double bond; i.e. 2-pentylidenecyclopentan-1-one, or with the less substituted cyclic double bond; i.e. 5-pentylcyclopent-2-en-1-one, were not observed.
[b)] Main product was 3-methyl-2-pentylcyclopent-2-en-1-one. Other regioisomers such as regioisomer with an exo double bond; i.e. 3-methyl-2-pentylidenecyclopentan-1-one or with the less substituted cyclic double bond; i.e. 4-methyl-5-pentylcyclopent-2-en-1-one, were not observed.
[c)] Main product was 2,6,6-trimethylcyclohex-2-en-1-one. Other regioisomers such as regioisomer with an exo double bond; i.e. 2,2-dimethyl-6-methylenecyclohexan-1-one, were not observed.
[d)] Main product was 2-ethyl-6,6-dimethylcyclohex-2-en-1-one. Other regioisomers such as regioisomer with an exo double bond; i.e. 6-ethylidene-2,2-dimethylcyclohexan-1-one, were not observed.
[e)] Main product was 2-ethyl-4,4-dimethylcyclohex-2-en-1-one. Other regioisomers such as regioisomer with an exo double bond; i.e. 2-ethylidene-4,4-dimethylcyclohexan-1-one or with the less substituted cyclic double bond; i.e. 6-ethyl-4,4-dimethylcyclohex-2-en-1-one, were not observed.
[f)] Main product was 2,3,8a-trimethyl-4a,5,6,7,8,8a-hexahydronaphthalen-1(4H)-one (mixture of diastereoisomers). Other regioisomers such as regioisomer with an exo double bond; i.e. 3,8a-dimethyl-2-methyleneoctahydronaphthalen-1(2H)-one were not observed.

Example 3

Dehydrogenation of 2-(3-Oxo-2-Pentylcyclopentyl)Acetate in the Presence of Oxygen—Comparative Example Experiment of example 1 was repeated with methyl 2-(3-oxo-2-pentylcyclopentyl)acetate as starting material but in the presence of oxygen. After similar treatment, the resulting oil was analyzed: the formation of methyl 2-(3-oxo-2-pentylcyclopent-1-en-1-yl)acetate was only 0.9%.

Dehydrogenation under oxygen as previously reported (U.S. Pat. No. 7,495,132 and *J. Org. Chem* 1971 752) leads to the formation of trace of desired product.

The invention claimed is:

1. A process for the preparation of a compound of formula (I)

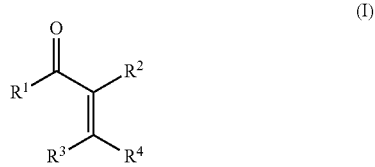

(I)

in a form of any one of its stereoisomers or a mixture thereof and wherein $R^1$, $R^2$ and $R^3$, simultaneously or independently, represent a linear or branched $C_{1-6}$ alkyl or alkenyl group or a linear $C_{2-5}$ alkynyl group, optionally comprising one or two functional groups selected amongst ether and ester; and $R^4$ represents a hydrogen atom, a linear or branched $C_{1-6}$ alkyl or alkenyl group or a linear $C_{2-5}$ alkynyl group, optionally comprising one or two functional groups selected amongst ether, and ester; $R^1$ and $R^3$, taken together, represent a $C_{2-9}$ alkanediyl or alkenediyl group optionally substituted by one to two linear or branched $C_{1-5}$ alkyl or $C_{2-5}$ alkenyl groups; or/and $R^2$ and $R^4$, taken together, represent a $C_{2-9}$ alkanediyl or alkenediyl group optionally substituted by one to five linear or branched $C_{1-5}$ alkyl or $C_{2-5}$ alkenyl groups; or/and $R^3$ and $R^4$, taken together, represent a $C_{2-9}$ alkanediyl or alkenediyl group optionally substituted by one to two linear or branched $C_{1-5}$ alkyl or $C_{2-5}$ alkenyl groups;

comprising the step of dehydrogenate compound of the formula (II)

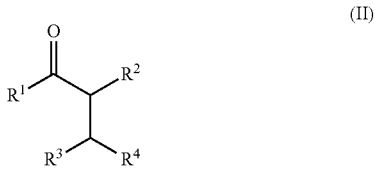

(II)

in a form of any one of its stereoisomers and wherein $R^1$, $R^2$, $R^3$, and $R^4$ have the same meaning as in formula (I);

said dehydrogenation being performed under an inert atmosphere in the presence of Palladium) ($Pd^0$) catalyst in elemental metallic form, wherein the reaction is carried out in the liquid phase.

2. The process according to claim 1, characterized in that the compound of formula (I) is compound of formula (III)

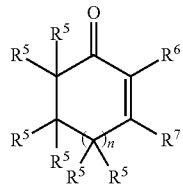

(III)

in a form of any one of its stereoisomers; wherein n is 0 or 1; $R^5$ groups represent, when taken separately, independently of each other, a hydrogen atom, a $C_{1-3}$ alkyl or alkenyl group; or two $R^5$ groups represent, when taken together, a $C_{1-5}$ alkanediyl or alkenediyl group optionally substituted by one to five linear $C_{1-3}$ alkyl groups; $R^6$ represents a linear or branched $C_{1-6}$ alkyl or alkenyl group or a linear $C_{2-5}$ alkynyl group, optionally comprising one or two functional groups selected amongst ether, and ester; $R^7$, represents a hydrogen atom, a linear or branched $C_{1-6}$ alkyl or alkenyl group or a linear $C_{2-5}$ alkynyl group, optionally comprising one or two functional groups selected amongst ether, and ester; $R^6$ and $R^7$, taken together, represent a $C_{2-9}$ alkanediyl or alkenediyl group optionally substituted by one to five linear or branched $C_{1-5}$ alkyl groups.

3. The process according to claim 1, characterized in that the compound of formula (II) is compound of formula (IV)

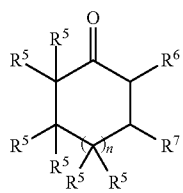

(IV)

in a form of any one of its stereoisomers; wherein n is 0 or 1; $R^5$ groups represent, when taken separately, independently of each other, a hydrogen atom, a $C_{1-3}$ alkyl or alkenyl group; or two $R^5$ groups represent, when taken together, a $C_{1-5}$ alkanediyl or alkenediyl group optionally substituted by one to five liner $C_{1-3}$ alkyl groups; $R^6$ represents a linear or branched $C_{1-6}$ alkyl or alkenyl group or a linear $C_{2-5}$ alkynyl group, optionally comprising one or two functional groups selected amongst ether, and ester; $R^6$ and $R^{7'}$ taken together, represent a $C_{2-9}$ alkanediyl or alkenediyl group optionally substituted by one to five linear or branched $C_{1-5}$ alkyl groups.

4. The process according to claim 1, characterized in that the compound of formula (I) is compound of formula (V)

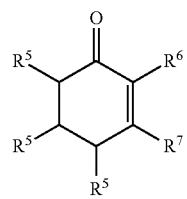

(V)

in a form of any one of its stereoisomers; wherein n is 0 or 1; $R^5$ represents a hydrogen atom, a $C_{1-3}$ alkyl or alkenyl group; $R^6$ represents a linear or branched $C_{1-6}$ alkyl or alkenyl group or a linear $C_{2-5}$ alkynyl group, optionally comprising one or two functional groups selected amongst ether, and ester; $R^7$, represents a hydrogen atom, a linear or branched $C_{1-6}$ alkyl or alkenyl group or a linear $C_{2-5}$ alkynyl group, optionally comprising one or two functional groups selected amongst ether, and ester; $R^6$ and $R^7$, taken together, represent a $C_{2-9}$ alkanediyl or alkenediyl group optionally substituted by one to five linear or branched $C_{1-5}$ alkyl groups.

5. The process according to claim 1, characterized in that the compound of formula (II) is compound of formula (IV)

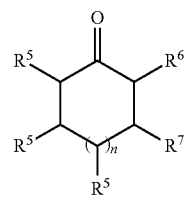

(IV)

in a form of any one of its stereoisomers; wherein n wherein n is 0 or 1; $R^5$ groups represent, when taken separately, independently of each other, a hydrogen atom, a $C_{1-3}$ alkyl or alkenyl group; or two $R^5$ groups represent, when taken together, a $C_{1-5}$ alkanediyl or alkenediyl group optionally substituted by one to five linear $C_{1-3}$ alkyl groups; $R^6$ represents a linear or branched $C_{1-6}$ alkyl or alkenyl group or a linear $C_{2-5}$ alkynyl group, optionally comprising one or two functional groups selected amongst ether, and ester; $R^7$, represents a hydrogen atom, a linear or branched $C_{1-6}$ alkyl or alkenyl group or a linear $C_{2-5}$ alkynyl group, optionally comprising one or two functional groups selected amongst ether, and ester; $R^6$ and $R^7$, taken together, represent a $C_{2-9}$ alkanediyl or alkenediyl group optionally substituted by one to five linear or branched $C_{1-5}$ alkyl groups.

6. The process according to claim 2, characterized in that n is 0.

7. The process according to claim 2, characterized in that $R^5$ represents a hydrogen atom, a methyl, an ethyl, a propyl an isopropyl or propen-2-yl group.

8. The process according to claim 2, characterized in that $R^5$ represents a hydrogen atom, a methyl an ethyl or propen-2-yl group.

9. The process according to claim 2, characterized in that $R^6$ represents a methyl, an ethyl, a propyl an isopropyl, a butyl, a pentyl, a pentenyl, a hexenyl, a 1-methoxy-1-oxoheptan-3-yl or 3-methylbut-2-en-1-yl group.

10. The process according to claim 2, characterized in that $R^6$ represents a methyl or pentyl group.

11. The process according to claim 2, characterized in that $R^7$ represents a hydrogen atom, a methyl, an ethyl or a propyl group or a $C_{1-3}$ alkyl acetate group.

12. The process according to claim 2, characterized in that $R^7$ represents a hydrogen atom, a methyl group or $C_{1-3}$ alkyl acetate group.

13. The process according to claim 3, characterized in that the compound of formula (IV) may be methyl 2-(3-oxo-2-pentylcyclopentyl)acetate, 3-methyl-2-pentylcyclopentan-1-one, 2-pentylcyclopentan-1-one, methyl 3-(2-oxocyclopentyl)heptanoate, 2,2,6-trimethylcyclohexan-1-one, 6-ethyl-2,2-dimethylcyclohexan-1-one, 2-ethyl-4,4- dimethylcyclohexan-1-one or 2,3,8a-trimethyloctahydronaphthalen-1(2H)-one.

14. The process according to claim 1, characterized in that the palladium) (Pd$^o$) is supported on a carrying material.

15. The process according to claim 1, characterized in that palladium is supported on aluminum oxide or charcoal.

16. The process according to claim 2, characterized in that R$^6$ represents a pentyl group.

* * * * *